(12) United States Patent
Noda

(10) Patent No.: US 9,220,471 B2
(45) Date of Patent: Dec. 29, 2015

(54) X-RAY DIAGNOSTIC APPARATUS

(75) Inventor: Kouji Noda, Nasushiobara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/524,512

(22) Filed: Jun. 15, 2012

(65) Prior Publication Data

US 2012/0257725 A1 Oct. 11, 2012

Related U.S. Application Data

(63) Continuation of application No. PCT/JP2011/068067, filed on Aug. 8, 2011.

(30) Foreign Application Priority Data

Aug. 18, 2010 (JP) ................................. 2010-183216
Aug. 5, 2011 (JP) ................................. 2011-172040

(51) Int. Cl.
A61B 6/00 (2006.01)

(52) U.S. Cl.
CPC .............. *A61B 6/4441* (2013.01); *A61B 6/4233* (2013.01)

(58) Field of Classification Search
CPC .................................................... A61B 6/4441
USPC ................................................. 378/197, 198
See application file for complete search history.

(56) References Cited

U.S. PATENT DOCUMENTS

| | | | | |
|---|---|---|---|---|
| 4,961,214 A * | 10/1990 | Van Endschot et al. | ...... | 378/197 |
| 5,386,453 A * | 1/1995 | Harrawood et al. | .......... | 378/196 |
| 5,425,068 A * | 6/1995 | Schaefer et al. | ............... | 378/197 |
| 6,132,087 A * | 10/2000 | Kusch et al. | ................... | 378/197 |
| 6,789,941 B1* | 9/2004 | Grady | .......................... | 378/197 |
| 7,462,832 B2* | 12/2008 | Ruehrnschopf | .......... | 250/363.07 |
| 2002/0126801 A1* | 9/2002 | Geelhoed et al. | ............. | 378/197 |

FOREIGN PATENT DOCUMENTS

| | | |
|---|---|---|
| CN | 2379095 Y | 5/2000 |
| CN | 1879561 A | 12/2006 |
| JP | 05-091609 | 12/1993 |
| JP | 2006-167300 A | 6/2006 |
| JP | 2008-086836 A | 4/2008 |

OTHER PUBLICATIONS

International Search Report issued Aug. 30, 2011 in Application No. PCT/JP2011/068067 (English Translation).
International Search Report issued Aug. 30, 2011 in PCT/JP2011/068067 filed Aug. 8, 2011.
Written Opinion issued Aug. 30, 2011 in PCT/JP2011/068067 filed Aug. 8, 2011.
English Translation of the International Preliminary Report on Patentability and Written Opinion issued Mar. 28, 2013 in PCT/JP2011/068067.
Chinese Office Action issued Nov. 28, 2013, in Chinese Patent Application No. 201180001773.6, filed Aug. 8, 2011 (with English-language translation).

* cited by examiner

*Primary Examiner* — Glen Kao
*Assistant Examiner* — Dani Fox
(74) *Attorney, Agent, or Firm* — Oblon, McClelland, Maier & Neustadt, L.L.P.

(57) ABSTRACT

In order to achieve reductions in the size and weight of an arm while ensuring the strength, an X-ray diagnostic apparatus includes an X-ray generation unit, an X-ray detection unit, an arm having an arch shape which supports the X-ray generation unit and the X-ray detection unit, and at least one reinforcing member which has a higher elastic modulus than the arm and a sheet-like shape and is fixed to the arm.

19 Claims, 8 Drawing Sheets

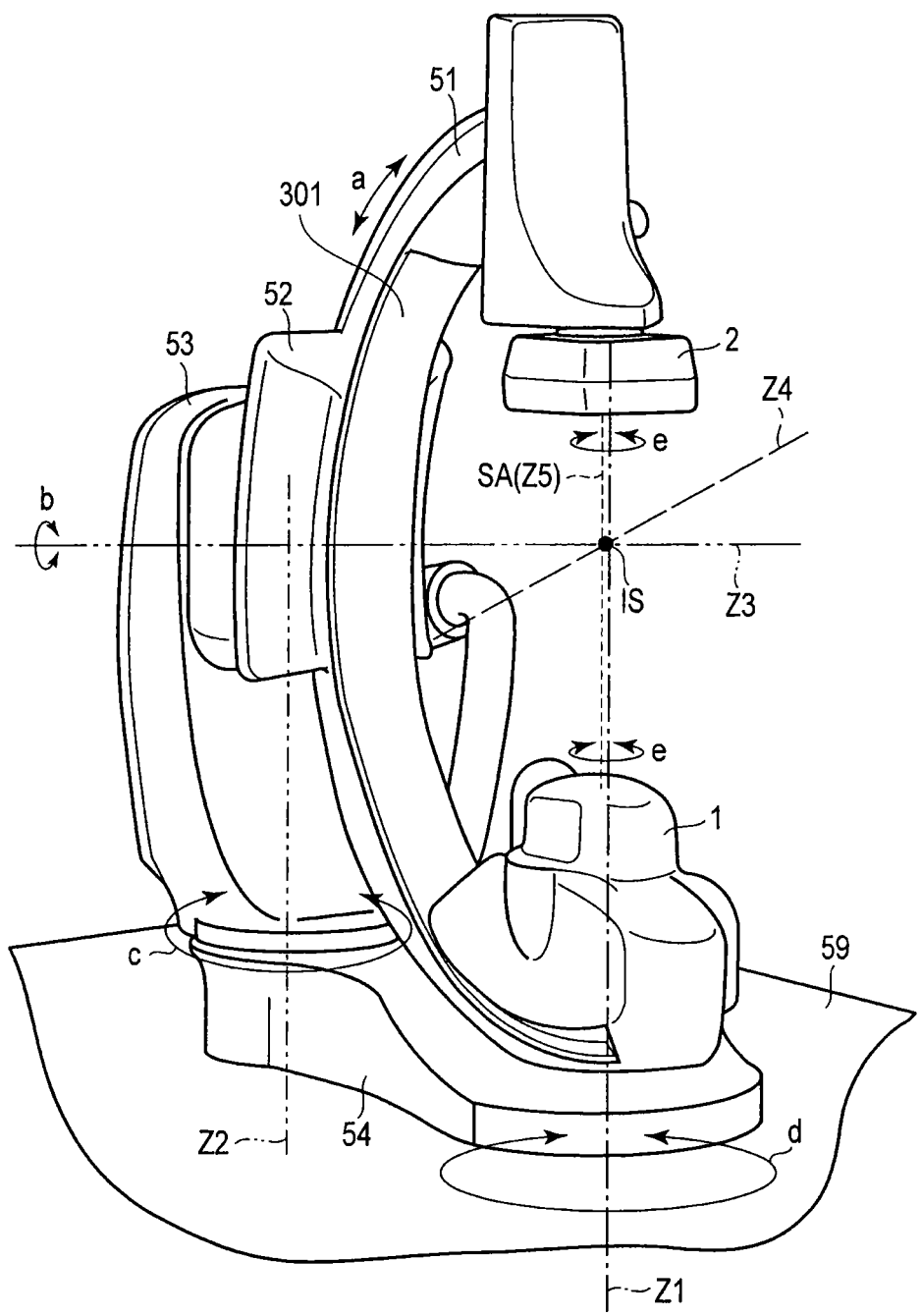
F I G. 1

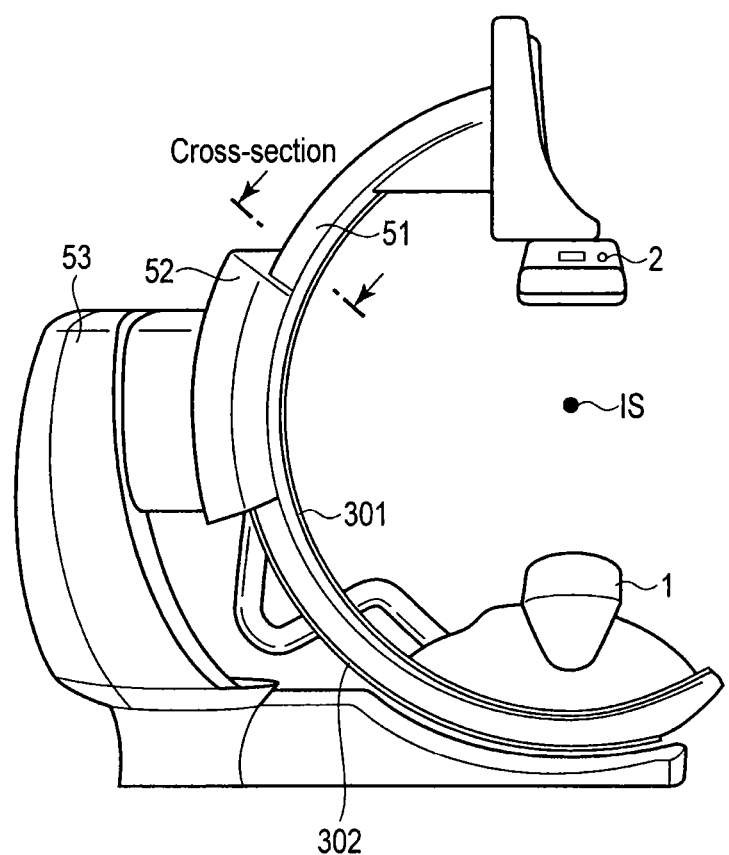
F I G. 5
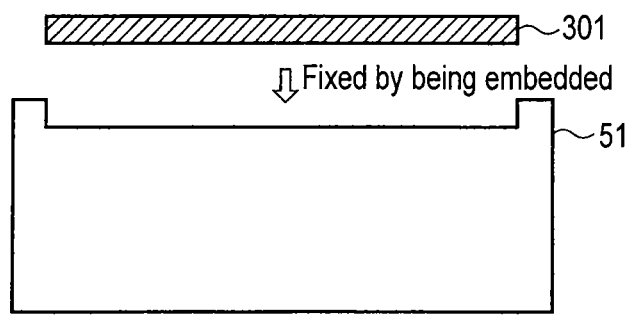
F I G. 6

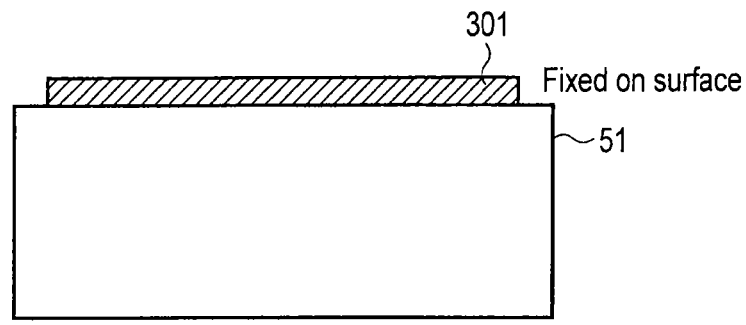
F I G. 7
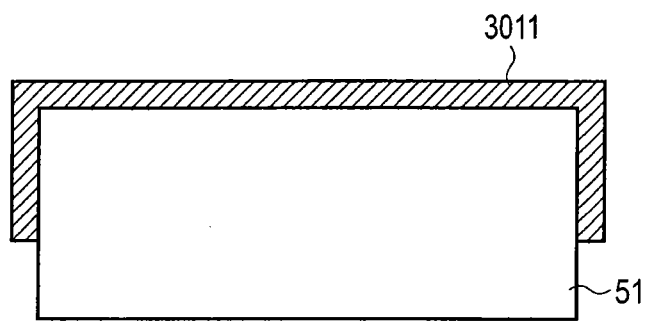
F I G. 8
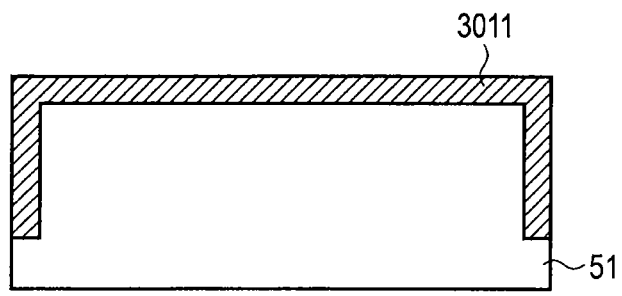
F I G. 9

X-RAY DIAGNOSTIC APPARATUS

CROSS REFERENCE TO RELATED APPLICATIONS

This application is a Continuation Application of PCT Application No. PCT/JP2011/068067, filed Aug. 8, 2011 and based upon and claiming the benefit of priority from prior Japanese Patent Applications No. 2010-183216, filed Aug. 18, 2010; and No. 2011-172040, filed Aug. 5, 2011, the entire contents of all of which are incorporated herein by reference.

FIELD

Embodiments described herein relate generally to an X-ray diagnostic apparatus.

BACKGROUND

Medical image diagnostic techniques using X-ray diagnostic apparatuses, MRI apparatuses, X-ray CT apparatuses, and the like have rapidly advanced with improvements in computer technology, and have become indispensable to current medical care.

Recently, X-ray diagnosis has advanced mainly in the field of circulatory organs with improvements in catheter techniques. An X-ray diagnostic apparatus for the diagnosis of circulatory organs generally includes an X-ray generation unit, an X-ray detection unit, a holding apparatus which holds the X-ray generation unit and the X-ray detection unit, a bed (top), a signal processing unit, and a display unit. The holding apparatus allows X-ray imaging at an optimal position or in an optimal direction by causing a C-arm or Ω arm pivot, rotate, or move around a patient (to be referred to as an object hereinafter).

The X-ray generation unit and the X-ray detection unit are mounted on the two ends of the C-arm in an arch shape so as to face each other. In order to prevent unnecessary exposure to X-rays and obtain accurate images, it is necessary in advance to match the X-ray center with the detector center. For this purpose, it is necessary to prevent positional shifts caused by the flexure of the C-arm by increasing its rigidity and ensuring the strength. However, with current needs for smaller, lighter apparatuses, it has become difficult to maintain necessary rigidity.

Recently, there have been increasing needs for smaller, lighter X-ray diagnostic apparatuses. In addition, there is a demand for reducing the thickness of the C-arm to decrease its height in the vertical direction while it is set in a vertical position. The thickness in this case indicates the length between the front surface (facing toward the isocenter) of the C-arm and the rear surface (located on the opposite side to the front surface). Further reducing the thickness can further reduce the total size of the apparatus including the C-arm.

In order to meet such needs, various studies have been made on materials for C-arms and their dimensions. Existing C-arms are aluminum extrudates or integrated products each made of a single material, manufactured by bending and welding a steel material. Owing to the physical property values of these members, it has become difficult to ensure necessary rigidity and strength.

BRIEF DESCRIPTION OF THE DRAWINGS

FIG. 1 is a perspective view of an X-ray diagnostic apparatus according to this embodiment;

FIG. 5 is a side view of the C-arm in FIG. 1;

FIG. 6 is a view showing an example of a method of fixing reinforcing members to the C-arm in FIG. 1;

FIG. 7 is a view showing another example of the method of fixing the reinforcing members to the C-arm in FIG. 1;

FIG. 8 is a view showing still another example of the method of fixing the reinforcing members to the C-arm in FIG. 1;

FIG. 9 is a view showing still another example of the method of fixing the reinforcing members to the C-arm in FIG. 1;

DETAILED DESCRIPTION

In general, according to one embodiment, an X-ray diagnostic apparatus comprises an X-ray generation unit; an X-ray detection unit; an arm having an arch shape which supports the X-ray generation unit and the X-ray detection unit; and at least one reinforcing member which has a higher elastic modulus than the arm and a sheet-like shape and is fixed to the arm.

An embodiment of the present invention will be described below with reference to the accompanying drawings.

Figure 2:
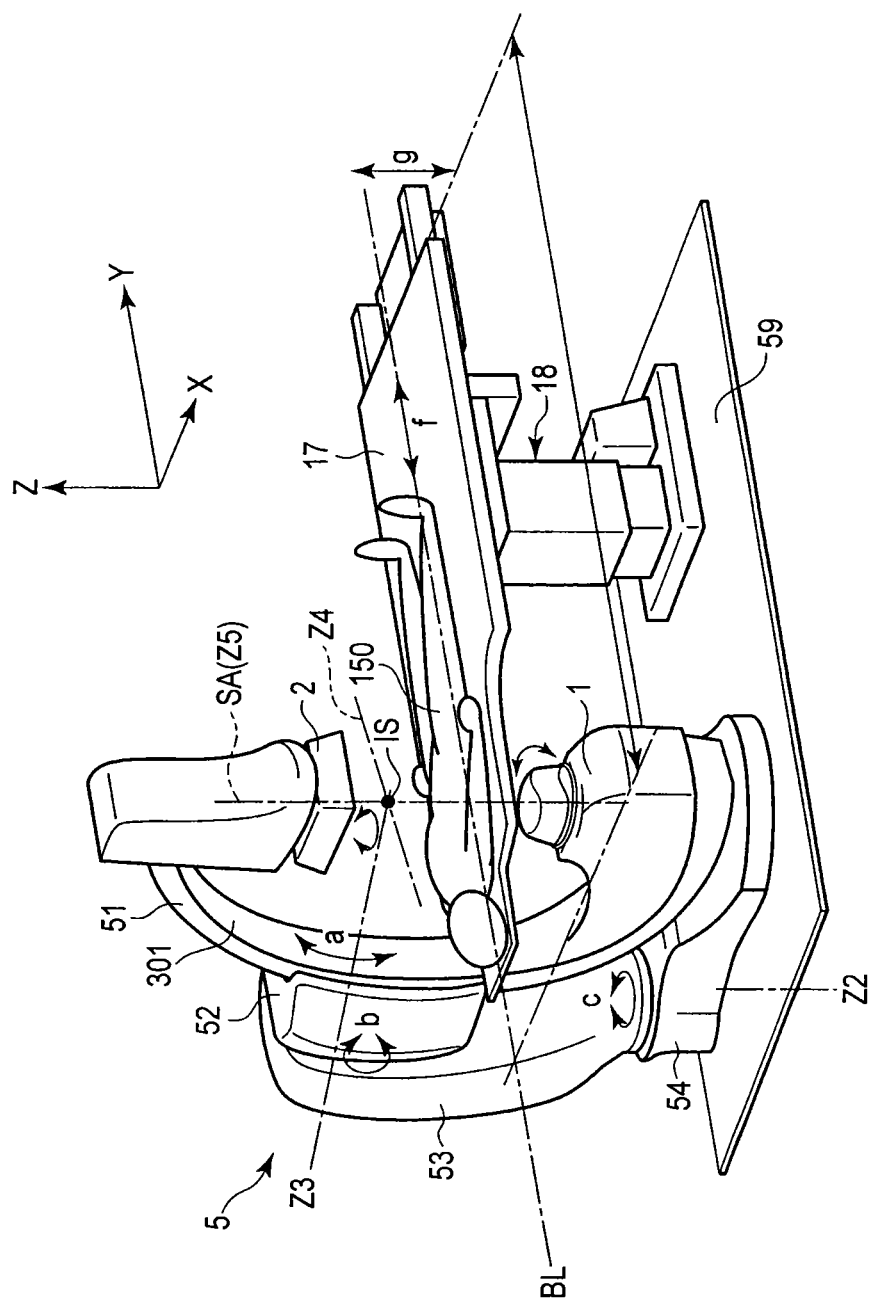
FIG. 2 is a perspective view of the X-ray diagnostic apparatus according to this embodiment.

As shown in FIGS. 1 and 2, a floor swing arm 54 is provided on a floor surface 59 so as to be swingable (d) about an almost perpendicular first rotation axis Z1 at one end of the arm. The first rotation axis Z1 is a vertical axis, which is perpendicular to a reference line BL. Note that at the time of imaging, an object 150 is placed on a top 17 such that the body axis of the object 150 almost coincides with the reference line BL. The reference line BL almost coincides with the central line of the top 17. The top 17 is provided on a bed 18 so as to be movable along a longitudinal direction parallel to the reference line BL. The first rotation axis Z1 intersects with the reference line BL within a movable range MR in the longitudinal direction of the top 17. That is, the floor swing arm 54 is provided within the movable range MR in the longitudinal direction of the top 17.

A stand 53 is supported on the other end of the floor swing arm 54 so as to be rotatable (c) about an almost vertical second rotation axis Z2. An arm holder 52 is supported on the stand 53 so as to be rotatable (b) about an almost horizontal third rotation axis (C-arm horizontal rotation axis) Z3. A C-arm 51 is supported on the arm holder 52 so as to be slidably rotatable about an almost horizontal fourth rotation axis (slide rotation axis) Z4 perpendicular to the C-arm horizontal rotation axis Z3. The C-arm 51 has an arch shape. The C-arm 51 typically has a C shape. A surface of the C-arm 51 which is located on the central side is called an inner surface or a front surface.

An X-ray generation unit 1 having an X-ray tube is mounted on one end of the C-arm 51. An X-ray detection unit (generally called a flat panel detector (FPD)) 2 having a plurality of X-ray detection semiconductor elements arranged two-dimensionally is mounted on the other end of the C-arm 51.

This apparatus is designed such that an imaging axis SA (Z5) passing through the X-ray focus of the X-ray generation unit 1 and the detection surface center of the X-ray detection unit 2 intersects with the C-arm horizontal rotation axis Z3 and the slide rotation axis Z4 at one point. As is known well, the absolute coordinates (the position on the imaging room coordinate system) of this intersection point do not displace unless the stand 53 rotates about the second rotation axis Z2 regardless of whether the C-arm 51 rotates about the C-arm horizontal rotation axis Z3, the C-arm 51 rotates about the slide rotation axis Z4, or the floor swing arm 54 swings about the first rotation axis Z1. This intersection point is generally called an isocenter IS.

As shown in FIG. 1, this apparatus is designed such that when the rotational angle of the stand 53 around the second rotation axis Z2 is a reference angle (0°) and the C-arm 51 overlaps the floor swing arm 54 and is folded to the smallest size, the isocenter is located on the first rotation axis Z1 of the floor swing arm 54, that is, the imaging axis SA (Z5), the C-arm horizontal rotation axis Z3, and the slide rotation axis Z4 intersect with the first rotation axis Z1 of the floor swing arm 54 at the isocenter. That is, the length of the floor swing arm 54, the size of the stand 53, the size of the arm holder 52, and the radius of the C-arm 51 are comprehensively determined so as to make the distance between the first rotation axis Z1 of the floor swing arm 54 and the second rotation axis Z2 of the stand 53 coincide with the distance between the second rotation axis Z2 of the stand 53 and the isocenter IS.

The C-arm 51 includes a support guide mechanism for implementing sliding operation in the arcuated direction. The C-arm 51 is manufactured using, as a material, an aluminum alloy or magnesium alloy which is lighter than steel and has a relatively high elastic modulus.

Assume that the rotational angle of the C-arm 51 around the C-arm horizontal rotation axis Z3 is a reference angle (0°), and the rotational angle of the C-arm 51 around the slide rotation axis Z4 is a reference angle (0°). In this state, when the imaging axis SA (Z5) is in the vertical direction, the imaging axis SA (Z5) almost coincides with the first rotation axis Z1 of the floor swing arm 54 while the rotational angle of the stand 53 around the second rotation axis Z2 is a reference angle (0°).

Figure 3:
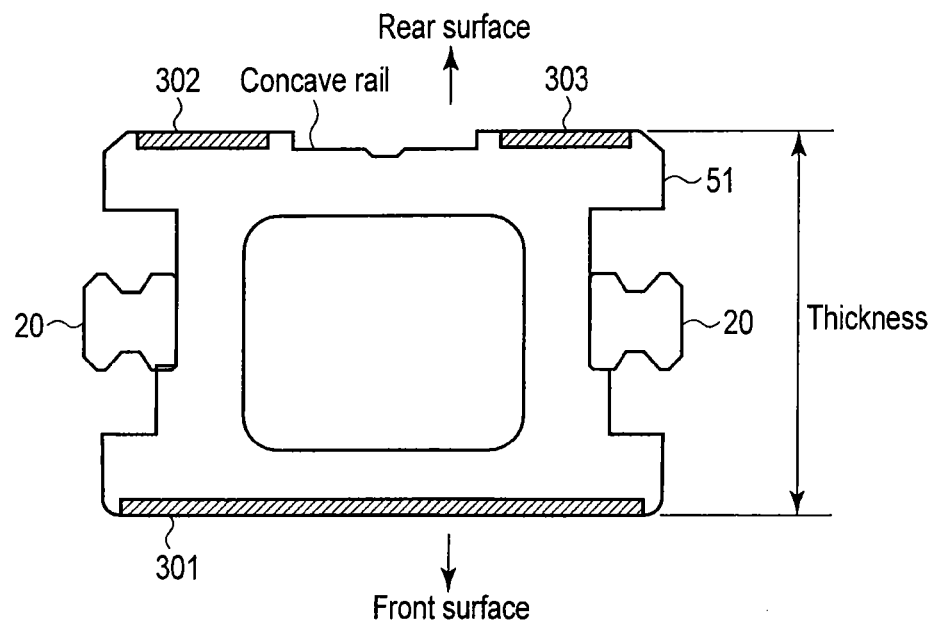
FIG. 3 is a cross-sectional view of a C-arm in FIG. 1.

FIG. 3 is a sectional view of the C-arm 51 according to this embodiment. The C-arm 51 is formed into an arch shape by using, for example, an aluminum alloy extrusion material. A support rail 20 is formed to support slidable rotation (a) around the slide rotation axis Z4. The support rail 20 is held by the arm holder 52 from the two end sides.

Reinforcing members 301, 302, and 303, each formed into a sheet-like shape, are fixed to the C-arm 51 with an adhesive or screws, or both. The C-arm 51 reinforced by the reinforcing members 301, 302, and 303 can achieve reductions in weight and size as compared with the C-arm made of only an aluminum alloy without any reinforcement while maintaining almost the same elastic modulus as that of the C-arm made of only an aluminum alloy without any reinforcement.

The reinforcing members 301, 302, and 303 have a higher elastic modulus than the C-arm 51. The reinforcing members 301, 302, and 303 are lower in mass per unit volume than the C-arm 51. The reinforcing members 301, 302, and 303 are manufactured using carbon fiber reinforced plastics (CFRP) or glass fiber reinforced plastics (GFRP).

As shown in FIGS. 3 and 5, the reinforcing member 301 is fixed to the inner surface (front surface) of the C-arm 51. The inner surface of the C-arm 51 indicates the surface of the C-arm 51 which is located on the arcuated central side. The reinforcing members 302 and 303 are fixed to the outer surface (rear surface) of the C-arm 51.

As shown in FIG. 7, the reinforcing member 301 is attached to the surface of the C-arm 51. The reinforcing members 302, 303 may be similarly attached to the surface of the C-arm 51. As shown in FIG. 6, the reinforcing member 301 may be fitted in recess portions of the C-arm 51. The reinforcing members 302, 303 may be similarly fitted in recess portions of the C-arm 51. The reinforcing members 301 may be embedded in the C-arm 51. The reinforcing member 301 may be sandwiched between layers of the C-arm 51 formed as a multilayer structure. As shown in FIGS. 8 and 9, the reinforcing member 3011 may be provided so as to cover the inner surface and portions of the side surfaces of the C-arm 51.

Figure 10:
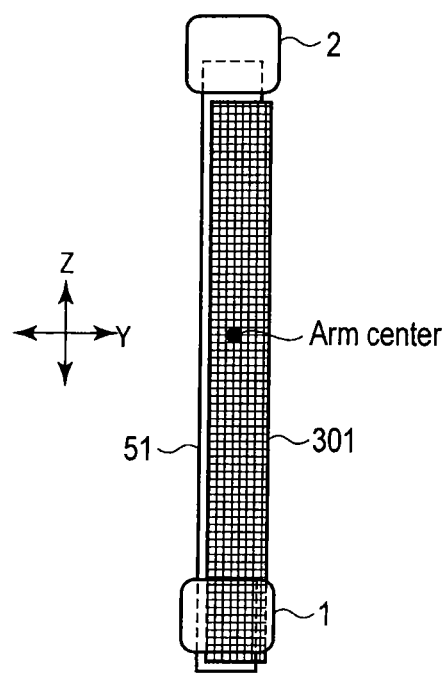
FIG. 10 is a view showing an example of the range in which a reinforcing member is attached to the C-arm in FIG. 1.
Figure 11:
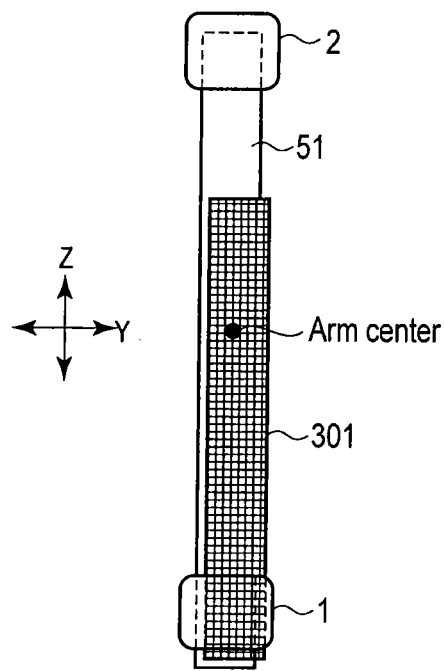
FIG. 11 is a view showing another example of the range in which a reinforcing member is attached to the C-arm in FIG. 1.
Figure 12:
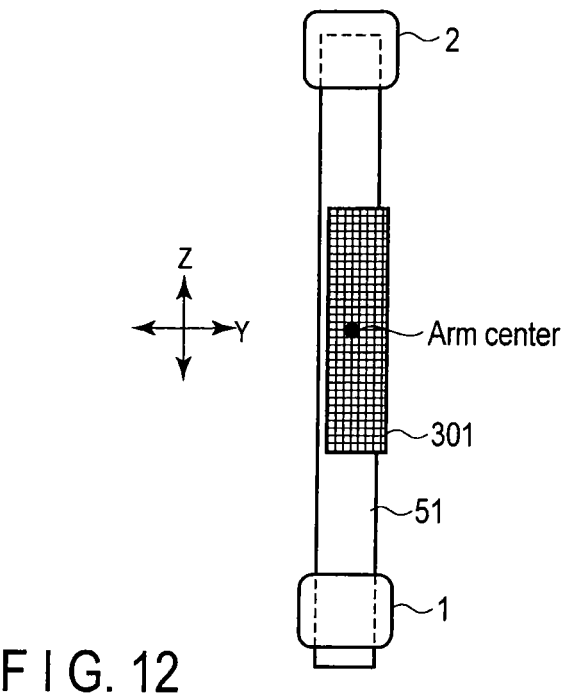
FIG. 12 is a view showing still another example of the range in which a reinforcing member is attached to the C-arm in FIG. 1.
Figure 13:
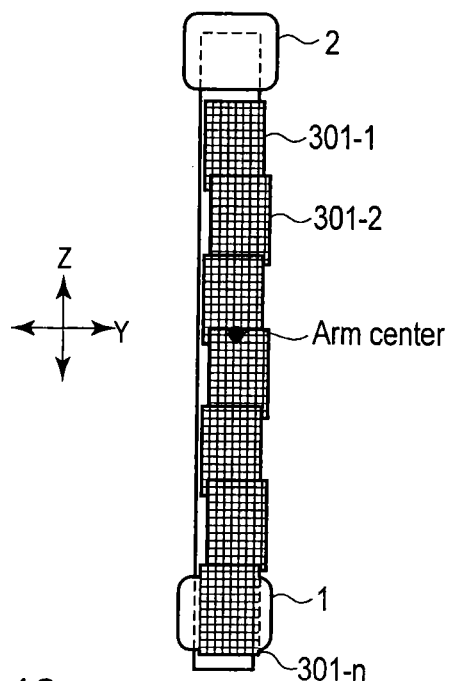
FIG. 13 is a view showing still another example of the range in which the reinforcing member is attached to the C-arm in FIG. 1.

As shown in FIGS. 10 and 11, the reinforcing member 301 is typically provided so as to extend from the position between the X-ray detection unit 2 and the center of the C-arm 51 to the position immediately below the X-ray generation unit 1 as a heavy load. Note that, as shown in FIG. 12, the reinforcing member 301 is provided on at least a portion of the C-arm 51 which includes its central portion on which the largest stress acts. As shown in FIG. 13, the reinforcing member 301 may be constituted by a plurality of reinforcing pieces 301-1, 301-2, . . . , 301-$n$ coupled in a column.

Figure 14:
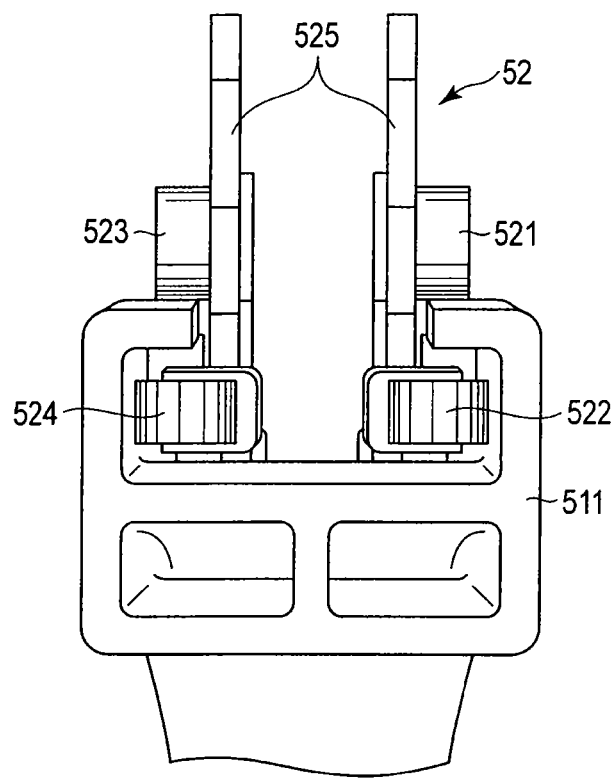
FIG. 14 is a cross-sectional view showing a structure designed to support the C-arm on the rear surface side by using a stand in FIG. 1.
Figure 15:
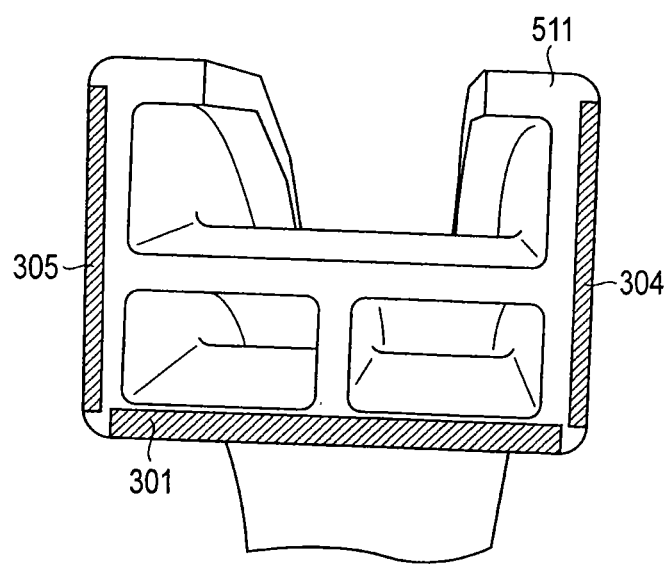
FIG. 15 is a cross-sectional view of the C-arm, showing the reinforcing members which reinforce the C-arm corresponding to the structure in FIG. 14 from the inner surface and side surfaces of the C-arm.

As shown in FIG. 14, the C-arm 51 may include a structure 511 which is supported on the rear surface of the C-arm 51 by the arm holder 52 using rollers 521 to 524. In this case, no reinforcing member can be provided on the rear surface of the C-arm 51. As shown in FIG. 15, reinforcing members 304 and 305 are provided on side surfaces of the C-arm 51.

The front surface of the C-arm 51 is a surface facing toward the isocenter, and the rear surface is a surface located on the opposite side to the front surface. A concave rail is formed in the rear surface of the C-arm 51 to accommodate a driving belt (not shown) for making the C-arm 51 rotate about the slide rotation axis Z4. For this reason, the reinforcing members 301, 302, and 303 are attached to the C-arm 51 so as not to interfere with the concave rail and the driving belt.

For example, physical property values associated with the rigidity and strength of CFRP can be expected to be about five or more times higher than aluminum in terms of longitudinal elastic modulus and about 10 or more times higher than aluminum in terms of tension strength. Even if, therefore, a carbon fiber reinforced material 30 is used partly, it is possible to increase the overall rigidity and strength of the C-arm 51 by intimately attaching and integrating the material with the C-arm 51 by bonding, press fitting, screw fastening, or the like.

Figure 4:
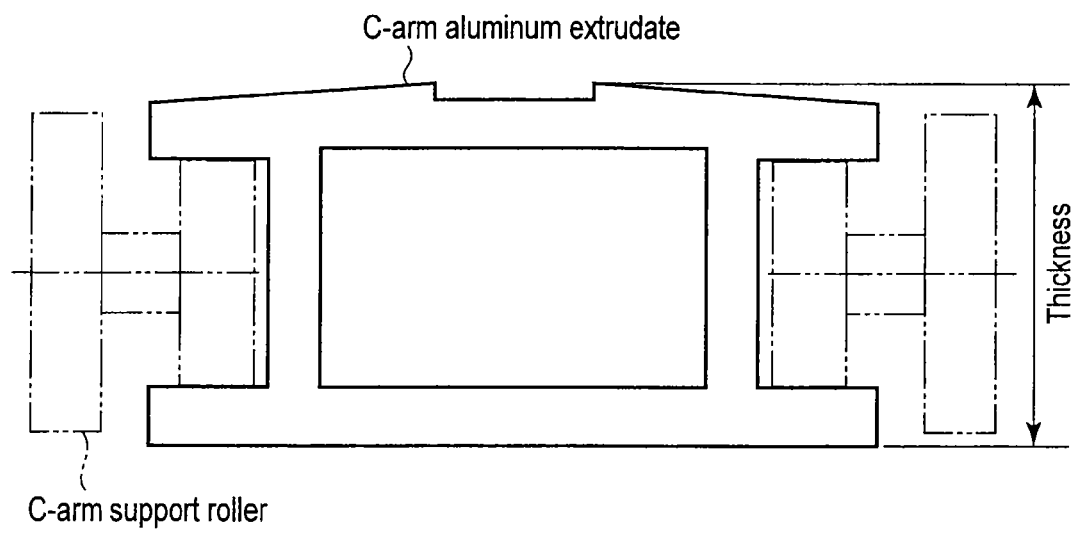
FIG. 4 is a cross-sectional view of a conventional C-arm.

This can increase the strength of the C-arm 51 and reduce the thickness, i.e., the length between the front surface and the rear surface, as compared with the case in which only a single aluminum composite base material is used. It is therefore possible to implement a C-arm holding apparatus smaller in size and weight than the conventional holding apparatus. The existing C-arm shown in FIG. 4 decreases in rigidity with a reduction in thickness, leading to flexure and distortion.

The C-arm has a support guide mechanism for implementing sliding operation in the arcuated direction. The general physical properties of a carbon fiber reinforced type composite resin material typified by CFRP are weaker than a base material in terms of contact pressure acting on the C-arm support guide portion. It is therefore necessary to use a material with a high allowable surface pressure, e.g., a metal or engineering plastic for the contact surface. That is, no fiber reinforced material can be used. In this embodiment, therefore, a carbon fiber reinforced material is bonded to a surface of the C-arm, formed by using aluminum or steel as a base material, other than the surface on which the support guide portion is formed. This makes it possible to increase the rigidity while reducing the size of the C-arm, and hence can implement an X-ray diagnostic apparatus smaller than size and weight than conventional apparatuses.

As has been described above, in this embodiment, in order to reduce the flexure of the C-arm 51 (improve the rigidity) while increasing the strength, aluminum or steel as a base material for the C-arm 51 is combined with a material having a higher longitudinal elastic modulus (Young's modulus), with these materials being formed into an integral structure by bonding, screw fastening, or the like. Using a material having a high longitudinal elastic modulus (Young's modulus), e.g., a material such as a carbon fiber reinforced resin (CFRP), can implement higher strength and rigidity than the base material. This can improve the rigidity and strength of the C-arm as an overall structure. It is therefore possible to reduce the sectional area of the C-arm while maintaining the strength. This makes it possible to achieve reductions in the size and weight of the C-arm.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
   an X-ray generation unit;
   an X-ray detection unit;
   an arm having an arch shape which supports the X-ray generation unit and the X-ray detection unit and having a concave rail on a part of the back of the arm;
   a supporting rail provided on the side of the arm to make the arm slide-able; and
   reinforcing members which have has a higher elastic modulus than the arm and a sheet-like shape, are fixed to a front of the arm and to the left and right of the concave rail on the back of the arm and do not surround the arm.

2. The X-ray diagnostic apparatus of claim 1, wherein the reinforcing member is fixed to an inner surface of the arm.

3. The X-ray diagnostic apparatus of claim 2, wherein the reinforcing member is provided so as to extend from a position between the X-ray detection unit and the center of the arm to a position immediately below the X-ray generation unit.

4. The X-ray diagnostic apparatus of claim 2, wherein the reinforcing members are provided both on the inner surface of the arm and the outer surface of the arm.

5. The X-ray diagnostic apparatus of claim 2, wherein the reinforcing members are provided both on the inner surface of the arm and a side surface of the arm.

6. The X-ray diagnostic apparatus of claim 2, wherein the reinforcing member is attached to an upper surface of the arm.

7. The X-ray diagnostic apparatus of claim 1, wherein the reinforcing member is fitted in a recess portion of the arm.

8. The X-ray diagnostic apparatus of claim 1, wherein the reinforcing member is embedded in the arm.

9. The X-ray diagnostic apparatus of claim 1, wherein the reinforcing member covers the inner surface and part of a side surface of the arm.

10. The X-ray diagnostic apparatus of claim 1, wherein the reinforcing member is fixed to the arm with an adhesive.

11. The X-ray diagnostic apparatus of claim 1, wherein the reinforcing member is fixed to the arm with a screw.

12. The X-ray diagnostic apparatus of claim 1, wherein the reinforcing member is made of a carbon fiber reinforced resin or a glass fiber reinforced resin, and the arm is made of an aluminum alloy or a magnesium alloy.

13. The X-ray diagnostic apparatus of claim 1, wherein the reinforcing member has a higher longitudinal elastic modulus than the arm.

14. The X-ray diagnostic apparatus of claim 1, wherein the arm has a C shape.

15. The X-ray diagnostic apparatus of claim 1, further comprising:
   a first support portion which rotatably supports the arm;
   a second support portion which rotatably supports the first support portion; and
   a floor support portion which swingably supports the second support portion.

16. The X-ray diagnostic apparatus of claim 1, further comprising:
   a first support portion which rotatably supports the arm;
   a second support portion which rotatably supports the first support portion; and
   a ceiling support portion which swingably supports the second support portion.

17. The X-ray diagnostic apparatus of claim 1, wherein the reinforcing member consists of one member having a u-shaped cross section attached to the inner surface of arm and side surfaces of the arm.

18. An X-ray diagnostic apparatus comprising:
   an X-ray generation unit;
   an X-ray detection unit;
   an arm having an arch shape which supports the X-ray generation unit and the X-ray detection unit; and
   at least one reinforcing member consisting of one member which has a higher elastic modulus than the arm and a sheet-like shape, and is attached to a surface of the arm only on a side that faces an isocenter of the X-ray diagnostic apparatus.

19. An X-ray diagnostic apparatus comprising:
   an X-ray generation unit;
   an X-ray detection unit;
   an arm having an arch shape which supports the X-ray generation unit and the X-ray detection unit; and
   a reinforcing member consisting of a first member which has a higher elastic modulus than the arm and a sheet-like shape and is attached to an inner surface of the arm, a second member which has a higher elastic modulus than the arm and a sheet-like shape and is attached to a first side surface of the arm, and a third member which has a higher elastic modulus than the arm and a sheet-like shape and is attached to a second side surface of the arm, the first, second and third members being separate from each other.

* * * * *